United States Patent [19]
Herrmann et al.

[11] Patent Number: 5,859,269
[45] Date of Patent: Jan. 12, 1999

[54] PROCESS FOR THE CONTINUOUS PRODUCTION OF MONOCARBOXYLIC ACIDS

[75] Inventors: Albert Thomas Herrmann, Brunsbüttel; Arnold Meyer, St. Michaelisdonn; Erich Scherf, Brunsbüttel; Clemens Schröder, Kayhude; Ansgar Reichenauer, Marne; Ernst Tönsen, Brunsbüttel, all of Germany

[73] Assignee: RWE-DEA Aktiengesellschaft fur Mineraloel und Chemie, Germany

[21] Appl. No.: 661,344

[22] Filed: Jun. 14, 1996

[30]       Foreign Application Priority Data

Jun. 16, 1995 [DE]   Germany ................ 195 21 900.7

[51] Int. Cl.⁶ ................................................. C07C 51/16
[52] U.S. Cl. ................................. 554/132; 554/156
[58] Field of Search ..................... 554/156, 132

[56]                References Cited

U.S. PATENT DOCUMENTS

| | | | |
|---|---|---|---|
| 3,558,678 | 1/1971 | Fanning et al. | 554/132 |
| 5,185,457 | 2/1993 | Carduck et al. | 554/71 |

FOREIGN PATENT DOCUMENTS

| | | |
|---|---|---|
| 0031694 | 7/1981 | European Pat. Off. . |
| 0249359 | 12/1987 | European Pat. Off. . |
| 4302463 | 8/1994 | Germany . |

*Primary Examiner*—Gary Geist
*Assistant Examiner*—Deborah D. Carr
*Attorney, Agent, or Firm*—Madan & Morris, PLLC

[57]                    ABSTRACT

A process for the continuous production of monocarboxylic acids from the corresponding alcohols by alkali fusion wherein the oxidation is continuously accomplished in an extrusion reactor without addition of diluents and the alkali salts of the monocarboxylic acids are discharged from the reactor as a solid product and are directly neutralised with mineral acids. High-purity monocarboxylic acids are obtained after phase separation.

17 Claims, No Drawings

PROCESS FOR THE CONTINUOUS PRODUCTION OF MONOCARBOXYLIC ACIDS

The instant invention relates to a process for the continuous production of linear and branched, saturated monocarboxylic acids having 6 to 48 carbon atoms. The linear or branched, primary alcohols are converted by alkali fusion, in the presence of alkali hydroxide and at elevated temperature, into the salts of such monocarboxylic acids. In a subsequent reaction step, the linear or branched monocarboxylic acids are obtained from the alkali salts by neutralisation.

The reaction product resulting from the aforementioned conversion, i.e. the $C_6$–$C_{48}$ monocarboxylic acids and the salts, esters or amides thereof, are suitable for a great number of applications, e.g. as textile additives, soaps, surfactants, solvents, plasticisers, hydraulic oils, lubricants and for epoxy and alkyd resins.

The oxidative production of carboxylic acid salts by alkali fusion has been known for many years. There are numerous publications found in patent literature describing improvements on the process under consideration. Due to the high temperatures of 200°–370° C. required for the reaction and the strongly oxidative environment produced by the alkali melt, reactors provided with special linings are required. The process liberates hydrogen which must be removed in an explosion-proof manner. The considerable generation of gas results in foaming of the reaction product which is difficult to handle, particularly difficult to agitate. In addition, the space-time yield decreases drastically.

The alkali salts are mostly added as aqueous solutions. The reaction optionally takes place in the presence of a catalyst, such as Zn or ZnO. As a result of the high temperatures required for the reaction, the reaction medium is dehydrated. The water thus obtained must be removed from the reactor, mostly together with the hydrogen. If no solvent is present, the alkali salt of the carboxylic acid will solidify into a paste-like material. By completion of the reaction, agitation and the exchange of materials will become difficult, thus preventing maximum conversion. After completion of the reaction yielding high conversions, it will be difficult to discharge the reaction product from the reactor and, furthermore, it will be impossible to discharge the product continuously.

EP 0 031 694-A1 describes a process in which an inert diluent, e.g. a mineral oil, is added. The product produced by said process is an emulsion of salt and mineral oil. After neutralisation, e.g. with mineral acids, resulting in separation of the aqueous phase from the organic phase, the resultant product phase has to be subjected to laborious purification in order to remove the inert diluent contaminating the product.

According to DE 43 02 463-A1, alkali hydroxide and Guerbet alcohols are reacted by batch reaction accomplished in an agitated reactor yielding the corresponding carboxylic acid salts. By completion of the reaction yielding high conversions, an inert diluent, preferably water, is sprayed into the reactor. The reaction mixture is cooled by the addition of water or the condensation of water in the dephlegmator and the viscosity is lowered. Thus, the reaction mixture is kept handleable in the agitated reactor. It is then possible to cleave the carboxylic acid salt with mineral acid. The space-time yield of the reaction in the agitated kettle is poor.

It is an object of the instant invention to eliminate the disadvantages of the prior art processes, i.e. low space-time yield, poor handling due to the high viscosity solidification of the carboxylic acid salt, and blocking of agitation or problematic discharge of the reaction product from the reactor, and, in particular, to provide a continuous process yielding high conversions in which no diluent or flow improver is needed and the hydrogen formed during the reaction is eliminated in a convenient manner in order to prevent foaming of the reaction product.

According to the instant invention, the problem is solved by a process for producing linear and branched, saturated monocarboxylic acids having 6 to 48 carbon atoms which comprises (A) converting linear or branched, primary alcohols into the alkali salts of the corresponding monocarboxylic acids in the presence of alkali hydroxide at elevated temperature and (B) liberating the linear or branched monocarboxylic acids from the alkali salts by neutralisation, wherein (a) the reaction of alkali hydroxide and alcohol is continuously carried out in a mixer reactor mixing the feedstock and transporting the materials from the inlet to the outlet (extrusion reactor) and (b) the feedstock is either fed in high concentrations or is concentrated during the reaction in the mixer by removal of water and/or any other diluent and hydrogen in the reaction zone such that the alkali salts of the corresponding monocarboxylic acids are discharged as pasty materials and the monocarboxylic acid is subsequently released from its salts by known neutralisation methods.

The pasty material discharged from the reactor may then be introduced directly into a mineral acid in order to liberate the carboxylic acids. It is preferred that the mineral acid be dilute sulfuric acid.

The alkali hydroxides, preferably NaOH and/or KOH, are preferably charged as a 50–86% by weight solution, in 0–40 mole % excess, preferably 20 mole %, relative to the alcohol quantity to be oxidised. They are charged together with the alcohol or separately to the front section of the extrusion reactor. The educts may be preheated to reaction temperature before being introduced into the reactor.

The reaction is preferably carried out at temperatures of max. 320° C., preferably 280°–300° C. The evaporating alcohol and the water originating from the feedstock may be eliminated from the extrusion reactor at one place or several places of the reaction zone, and the condensed alcohol may be recharged to the reactor at one place or several places of the reaction zone. In addition, the hydrogen formed during the reaction is continuously removed from the reactor at one place or several places of the reaction zone. The oxidation in the alkali melt may be accomplished under pressure, e.g. at pressures of up to 30 bar, particularly 2–6 bar.

In order to limit the reactor length and to reduce the residence time it will be advantageous to partially react the alcohol (about 30–70%) with a 50–86% aqueous alkali hydroxide solution and to charge the incompletely reacted product to the mixer reactor to which further quantities of alkali hydroxide may then be added. Said preliminary reaction may be carried out at pressures of up to 30 bar, preferably 2 to 6 bar, and at temperatures of up to 320° C., preferably 280°–300° C.

To prevent thickening of the feedstock during the preliminary reaction which should be carried out advantageously in a conventional agitated reactor, the alkali hydroxide may be added in hypomolar quantities.

The water which is present at the beginning of the reaction or any other diluent added, for instance during the preliminary reaction, must be eliminated before introducing the feedstock into the mixer reactor. Alternatively, the reaction mixture may be freed from the diluent when passing through the reaction zone of the mixer reactor, preferably at the beginning, such that the reaction mixture will form a highly viscous, paste-like material at an early stage of the process.

The mixer reactor may be a single-shaft kneader reactor, but it is preferred that the reactor be a twin-screw extruder allowing to reduce the average residence times by a factor of 5, i.e. less than 2 hours, in comparison with a single-shaft kneader reactor. The average residence time required for optimum conversion in a twin-screw extruder is normally 1 hour or less. Since the reaction temperatures are high it is essential that the mixer reactor be alkali-resistant. For instance, a nickel reactor would be appropriate.

All the process steps, including preliminary reaction and neutralisation of the carboxylic acid alkali salt, are accomplished continuously.

EXAMPLES

Example 1

Preparation of 2-Butyl-Caprylic Acid

2-Butyloctanol (2 kgs/h) and 85% KOH pellets (0.99 kg/h) were reacted in a continuously operated, horizontal single-shaft kneader reactor maintained at a temperature of 320° C. and a pressure above atmospheric of 6 bar. The solid potassium hydroxide was continuously charged via a valve system. The hydrogen formed during the reaction was controlled by means of a pressure relief valve and was measured by means of a gas meter. The average residence time in the reaction apparatus was 5 hours. The paste-like alkali soap was removed via a twin-shaft discharge screw flanged to the outlet and discharging the soap into a stirred vessel. Neutralisation was accomplished under agitation and at a temperature of 80° C. using a 10% sulfuric acid. 2-Butyl-caprylic acid was obtained as an organic phase which was separated from the aqueous phase. The average residence time was ≦15 minutes. The 2-butyl-caprylic acid had a purity of ≧95%.

Analytical Data

| Acid number | [mg KOH/g] | 270–290 |
|---|---|---|
| Ester number | [mg KOH/g] | max. 3.0 |
| Iodine number | [mg 1/100 mg] | max. 2.0 |
| Water | [%] | max. 0.1 |
| Colour number | [Hazen] | max. 30 |
| Density at 20° C. | [g/ml] | 0.887 |
| Refractive index at 20° C. | | 1.4394 |
| Melting range | [°C.] | –14 to –10 |

Example 2

Preparation of 2-Octyl-Dodecanoic Acid

2-Octyl-docecanol (5 kgs/h) and a 50% aqueous potassium hydroxide solution (0.94 kg/h) were partially reacted in a continuously operated stirred reactor maintained at a temperature of 320° C. and a pressure above atmospheric of 2 bar. The soap/alcohol mixture obtained after a reaction time of 0.5 hour was charged at a rate of 5.44 kgs/h to a continuously operated twin-screw extruder connected in series. The remaining 50% aqueous potassium hydroxide solution was charged to the extruder at a rate of 1.32 kgs/h. The conversion into soap was completed under intensive mixing and kneading. The conversion rate was ≧95%. The residence time in the 40 D extruder was ≦0.3 h at normal pressure and a temperature of 320° C. The hydrogen formed and the steam from the alkaline solution were removed via a manifold, while entrained alcohol was returned to the reaction zone. The hydrogen quantity was measured by means of a gas meter in order to monitor the reaction.

A pasty soap was obtained at the outlet of the extruder. The soap dropped through a pipe into a stirred vessel connected in series. The neutralisation of the alkali salt was accomplished under agitation and at a temperature of 80° C. using a 10% sulfuric acid. 2-Octyl-dodecanoic acid was obtained as an organic phase which was separated from the aqueous phase. The residence time was ≦15 minutes.

The 2-octyl-dodecanoic acid had a purity of ≧97.5%.

Analytical Data

| Acid number | [mg KOH/g] | 170–190 |
|---|---|---|
| Ester number | [mg KOH/g] | max. 3.0 |
| Iodine number | [mg 1/100 mg] | max. 2.0 |
| Water | [%] | max. 0.1 |
| Colour number | [Hazen] | max. 30 |
| Density at 60° C. | [g/ml] | 0.846 |
| Refractive index at 60° C. | | 1.444 |
| Melting range | [°C.] | 34–35 |

Example 3

Preparation of 1-Hexanoic Acid

1-Hexanol (1 kg/h) was charged to a continuously operated twin-screw extruder to which 85% potassium hydroxide pellets (0.9 kg/h) were continuously added via a valve system. The conversion into soap was accomplished under intensive mixing and kneading. The conversion rate was ≧95%. The residence time in the 40 D extruder was ≦0.9 h at a temperature of 320° C. and a pressure of 27 bar. The hydrogen formed and the steam from the alkali hydroxide were removed via a manifold, while entrained alcohol was returned to the reaction zone. The hydrogen quantity was measured by means of a gas meter in order to monitor the reaction.

A solid soap was obtained at the outlet of the extruder. The soap dropped through a pipe into a stirred vessel connected in series. The neutralisation of the alkali salt was accomplished under agitation and at a temperature of 80° C. using a 10% sulfuric acid. 1-Hexanoic acid was obtained as an organic phase which was separated from the aqueous phase. The residence time was ≦5 minutes.

The 1-hexanoic acid had a purity of ≧98%.

Analytical Data

| Acid number | [mg KOH/g] | 470–490 |
|---|---|---|
| Ester number | [mg KOH/g] | max. 3.0 |
| Iodine number | [mg 1/100 mg] | max. 2.0 |
| Water | [%] | max. 0.1 |
| Colour number | [Hazen] | max. 10 |
| Density at 20° C. | [g/ml] | 0.9286 |
| Refractive index at 20° C. | | 1.416 |
| Melting range | [°C.] | –2 to –1 |

Example 4

Preparation of 1-Docosanoic Acid

1-Docosanol (10 kgs/h) was charged to a continuously operated twin-screw extruder to which 85% potassium hydroxide pellets (2.8 kgs/h) were continuously added via a valve system. The conversion into soap was accomplished under intensive mixing and kneading. The conversion rate was ≧95%. The residence time in the 40 D extruder was ≦0.2 h at a temperature of 320° C. The hydrogen formed and the steam from the alkali hydroxide were removed via a manifold, while entrained alcohol was returned to the reaction zone. The hydrogen quantity was measured by means of a gas meter in order to monitor the reaction. A pasty soap was obtained at the outlet of the extruder. The soap dropped through a pipe into a stirred vessel connected in series. The neutralisation of the alkali salt was accomplished under agitation and at a temperature of 90° C. using a 10% sulfuric acid. 1-Docosanoic acid was obtained as an organic phase which was separated from the aqueous phase. The residence time was ≦20 minutes.

The 1-docosanoic acid had a purity of ≧95%.
Analytical Data

| Acid number | [mg KOH/g] | 155–170 |
| Ester number | [mg KOH/g] | max. 3.0 |
| Iodine number | [mg 1/100 mg] | max. 2.0 |
| Water | [%] | max. 0.1 |
| Colour number | [Hazen] | max. 100 |
| Density at 90° C. | [g/ml] | 0.8225 |
| Refractive index at 90° C. | | 1.4263 |
| Melting range | [°C.] | 78–80 |

Example 5

Preparation of 2-Hexadecyl-Eicosanoic Acid

2-Hexadecyleicosanol (10 kgs/h) was charged to a continuously operated twin-screw extruder to which 85% potassium hydroxide pellets (1.75 kgs/h) were continuously added via a valve system. The conversion into soap was accomplished under intensive mixing and kneading. The conversion rate was ≧95%. The residence time in the 40 D extruder was ≦0.2 h at a temperature of 320° C. The hydrogen formed and the steam from the alkali hydroxide were removed via a manifold, while entrained alcohol was returned to the reaction zone. The hydrogen quantity was measured by means of a gas meter in order to monitor the reaction.

A pasty soap was obtained at the outlet of the extruder. The soap dropped through a pipe into a stirred vessel connected in series. The neutralisation of the alkali salt was accomplished under agitation and at a temperature of 90° C. using a 10% sulfuric acid.

2-Hexadecyl-eicosanoic acid was obtained as an organic phase which was separated from the aqueous phase. The residence time was ≦25 minutes.

The 2-hexadecyl-eicosanoic acid had a purity of 90%.
Analytical Data

| Acid number | [mg KOH/g] | 470–490 |
| Ester number | [mg KOH/g] | max. 3.0 |
| Iodine number | [mg 1/100 mg] | max. 2.0 |
| Water | [%] | 0.1 |
| Colour number | [Hazen] | max. 200 |
| Density at 80° C. | [g/ml] | 0.826 |
| Refractive index at 80° C. | | 1.4414 |
| Melting range | [°C.] | 70–74 |

Example 6

Preparation of 2-Butyl-Caprylic Acid

2-Butyloctanol (1 kg/h) and a 50% potassium hydroxide solution (0.84 kg/h) were reacted in a continuously operated twin-screw extruder maintained at a temperature of 320° C. and a pressure above atmospheric of 6 bar. The hydrogen formed during the reaction was controlled by means of a pressure relief valve and was measured by means of a gas meter. The average residence time in the reaction apparatus was about 1 hour. The paste-like alkali soap was removed through a pipe flanged to the outlet and was discharged into a stirred vessel connected in series. Neutralisation was accomplished under agitation and at a temperature of 80° C. using a 10% sulfuric acid. 2-Butyl-caprylic acid was obtained as an organic phase which was separated from the aqueous phase. The average residence time was ≧15 minutes.

The 2-butyl-caprylic acid had a purity of ≧95%.
Analytical data

| Acid number | [mg KOH/g] | 270–290 |
| Ester number | [mg KOH/g] | max. 3.0 |
| Iodine number | [mg 1/100 mg] | max. 2.0 |
| Water | [%] | max. 0.1 |
| Colour number | [Hazen] | max. 30 |
| Density at 20° C. | [g/ml] | 0.887 |
| Refractive index at 20° C. | | 1.4394 |
| Melting range | [°C.] | −14 to −10 |

We claim:

1. A continuous process for producing linear or branched, saturated monocarboxylic acids having from 6 to 48 carbon atoms, which comprises:
   (A) converting linear or branched, primary alcohols into alkali salts of the corresponding monocarboxylic acids in the presence of an alkali hydroxide at elevated temperatures comprising:
      (a) continuously reacting a feedstock consisting essentially of the alkali hydroxide and the alcohols in an extrusion reactor by mixing the feedstock and transporting the materials from the inlet to the outlet, where the alkali hydroxide is a 50 to 86% aqueous alkali hydroxide, and where the alkali hydroxide is present in a molar excess up to 40%, relative to the alcohol quantity; and
      (b) maintaining high concentration of the feedstock by a method selected from the group consisting of:
         (i) feeding the feedstock in high concentration, and
         (ii) removing hydrogen and any diluent from the feedstock and the extrusion reactor;
      such that the alkali salts of the corresponding monocarboxylic acids are discharged from the extrusion reactor as pasty materials;
   (B) liberating the linear or branched, saturated monocarboxylic acids from the alkali salts by neutralisation.

2. A process according to claim 1 wherein the pasty materials discharged from the reactor are directly introduced into a mineral acid in order to liberate the carboxylic acids.

3. A process according to claim 1 wherein the aqueous alkali hydroxide used in stage (A) of the process is selected from the group consisting of NaOH and KOH.

4. A process according to claim 1 wherein the reaction is carried out at elevated temperatures no higher than 320° C.

5. A process according to claim 1 wherein evaporating alcohol and the diluent originating from the feedstock are removed from the extrusion reactor at at least one place, are condensed, and wherein the alcohol is returned to the reactor at at least one place.

6. A process according claim 1 wherein the hydrogen formed during the reaction is continuously removed from more than one place on the extrusion reactor.

7. A process according to claim 1 wherein step (A) of the process is performed at an excess pressure of up to 30 bar.

8. A process according to claim 1 wherein the reaction is carried out in a twin-screw extruder and the average residence time in said twin-screw extruder is approximately 1 hour or less.

9. A process according to claim 1 wherein the alcohols are partially reacted to an extent of about 30 to 70% by preliminary reaction with a 50 to 86% aqueous solution of the alkali hydroxide to produce an incompletely reacted product and the incompletely reacted product is charged to the extrusion reactor to which further quantities of alkali hydroxide are then added.

10. A process according to claim 9 wherein the preliminary reaction is carried out at an excess pressure of up to 30 bar.

11. A process according to claim 9 wherein the preliminary reaction is carried out at a elevated temperature no higher than 320° C.

12. A process according to claim 9 wherein for the preliminary reaction the alkali hydroxide is added in hypomolar quantities, relative to the alcohol quantity.

13. A process according to claim 1, where a preliminary reaction of the alcohols with an alkali hydroxide is present prior to step (A), and wherein all the process steps, including preliminary reaction and neutralisation of the alkali salts, are performed continuously.

14. A continuous process for producing linear or branched, saturated monocarboxylic acids having from 6 to 48 carbon atoms, which comprises:
   (A) converting linear or branched, primary alcohols into alkali salts of the corresponding monocarboxylic acids in the presence of an alkali hydroxide selected from the group consisting of NaOH and KOH, at elevated temperatures no higher than 320° C., and at an excess pressure of up to 30 bar, comprising:
      (a) continuously reacting a feedstock consisting essentially of the alkali hydroxide and the alcohols in an extrusion reactor by mixing the feedstock and transporting the materials from the inlet to the outlet, where the alkali hydroxide is a 50 to 86% aqueous alkali hydroxide, and where the alkali hydroxide is present in a molar excess up to 40%, relative to the alcohol quantity; and
      (b) maintaining high concentration of the feedstock by a method selected from the group consisting of:
         (i) feeding the feedstock in high concentration, and
         (ii) removing hydrogen and any diluent from the feedstock and the extrusion reactor;
         such that the alkali salts of the corresponding monocarboxylic acids are discharged from the extrusion reactor as pasty materials;
   (B) liberating the linear or branched, saturated monocarboxylic acids from the alkali salts by neutralisation.

15. A process according to claim 14 wherein the aqueous alkali hydroxide used in stage (A) of the process is selected from the group consisting of NaOH and KOH.

16. A process according to claim 14 wherein the reaction is carried out in a twin-screw extruder and the average residence time in said twin-screw extruder is approximately 1 hour or less.

17. A continuous process for producing linear or branched, saturated monocarboxylic acids having from 6 to 48 carbon atoms, which comprises:
   (A) converting linear or branched, primary alcohols into alkali salts of the corresponding monocarboxylic acids in the presence of an alkali hydroxide selected from the group consisting of NaOH and KOH, at elevated temperatures no higher than 320° C., and at an excess pressure of up to 30 bar, where the feedstock consists essentially of the alcohols and the alkali hydroxide, comprising:
      (a) partially reacting the alcohols to an extent of about 30 to 70% by preliminary reaction of the alcohols with a 50 to 86% aqueous solution of the alkali hydroxide to produce an incompletely reacted product,
      (b) continuously reacting the incompletely reacted product in an extrusion reactor by mixing the product with additional alkali hydroxide, and transporting the materials from the inlet to the outlet, where the alkali hydroxide is present in a molar excess up to 40%, relative to the alcohol quantity; and
      (c) maintaining high concentration of the feedstock by a method selected from the group consisting of:
         (i) feeding the feedstock in high concentration, and
         (ii) removing hydrogen and any diluent from the feedstock and the extrusion reactor;
         such that the alkali salts of the corresponding monocarboxylic acids are discharged from the extrusion reactor as pasty materials;
   (B) liberating the linear or branched, saturated monocarboxylic acids from the alkali salts by neutralisation with a mineral acid.

* * * * *